United States Patent
Jugl et al.

(10) Patent No.: US 9,345,832 B2
(45) Date of Patent: May 24, 2016

(54) CARTRIDGE HOLDER AND DRUG DELIVERY DEVICE

(75) Inventors: Michael Jugl, Frankfurt am Main (DE); Axel Teucher, Frankfurt am Main (DE); Kerstine Hemmann, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 646 days.

(21) Appl. No.: 13/509,008

(22) PCT Filed: Dec. 1, 2010

(86) PCT No.: PCT/EP2010/068595
§ 371 (c)(1),
(2), (4) Date: Dec. 28, 2012

(87) PCT Pub. No.: WO2011/067269
PCT Pub. Date: Jun. 9, 2011

(65) Prior Publication Data
US 2013/0102972 A1    Apr. 25, 2013

(30) Foreign Application Priority Data
Dec. 2, 2009 (EP) ..................................... 09177684

(51) Int. Cl.
*A61M 5/24* (2006.01)
*A61M 5/34* (2006.01)

(52) U.S. Cl.
CPC ............... *A61M 5/24* (2013.01); *A61M 5/2466* (2013.01); *A61M 5/347* (2013.01)

(58) Field of Classification Search
CPC ........ A61M 5/24; A61M 5/2466; A61M 5/347
USPC .................. 604/187, 200–201, 232, 240–241
See application file for complete search history.

(56) References Cited

U.S. PATENT DOCUMENTS 5,693,027 A * 12/1997 Hansen et al. ................ 604/232

FOREIGN PATENT DOCUMENTS

WO            9916487  A1    4/1999
WO    WO 2008008694 A2  *  1/2008

OTHER PUBLICATIONS

Form PCT/IPEA/416, Notification of Transmittal of the International Preliminary Report on Patentability.

* cited by examiner

*Primary Examiner* — Theodore Stigell
*Assistant Examiner* — Amber Stiles
(74) *Attorney, Agent, or Firm* — McDonnell Boehnen Hulbert & Berghoff LLP

(57) ABSTRACT

A cartridge holder for a drug delivery device. The cartridge holder comprises a proximal portion for receiving a cartridge filled with a medicinal fluid to be dispensed by the drug delivery device, and a distal portion comprising a mount for a piercing assembly. The piercing assembly is adapted to provide a fluid-transferring connection with the inner volume of the cartridge by way of a piercing element pointing in distal direction with a pointed free end section. Retaining means adapted to substantially prevent the cartridge from displacing in proximal direction with respect to the proximal portion distal portion.

12 Claims, 2 Drawing Sheets

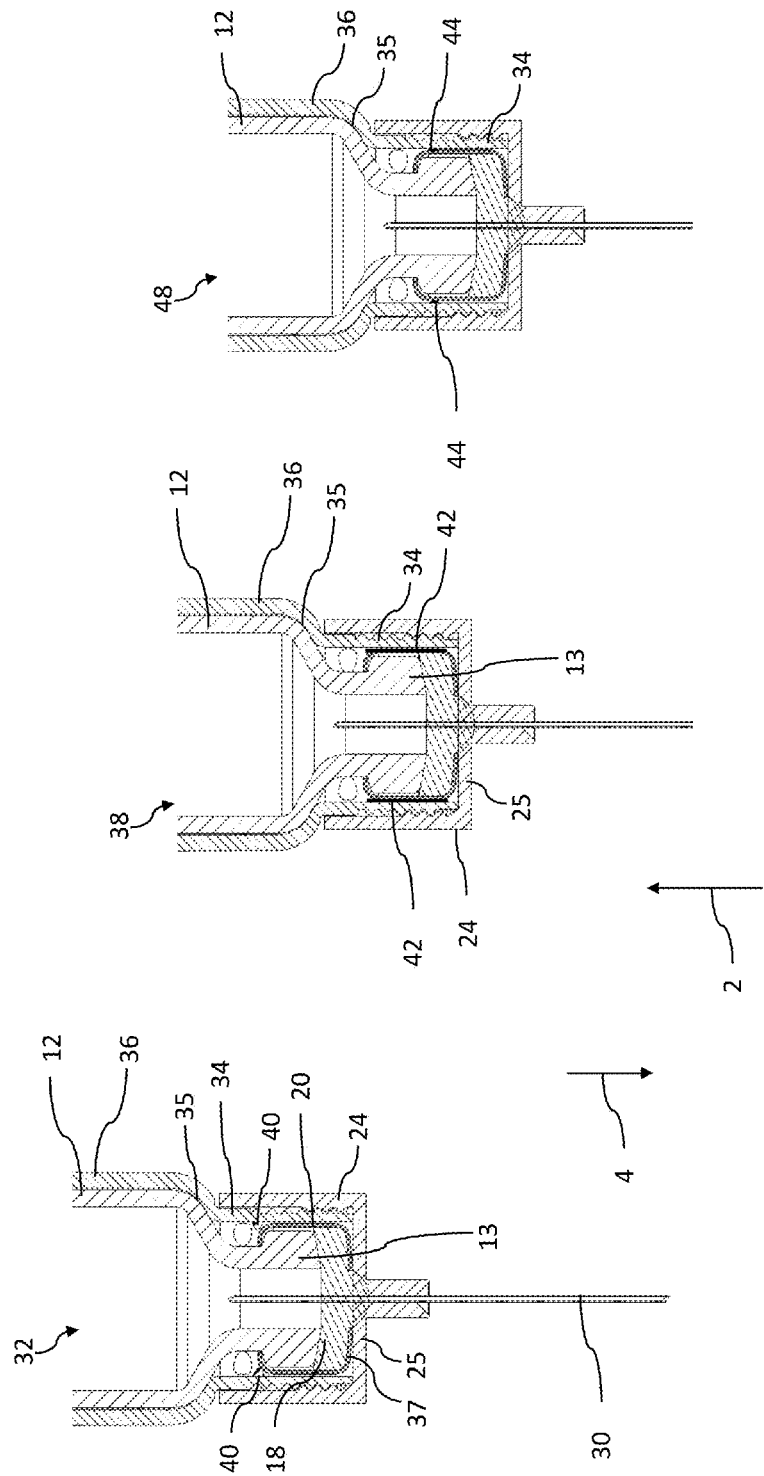

CARTRIDGE HOLDER AND DRUG DELIVERY DEVICE

CROSS REFERENCE TO RELATED APPLICATIONS

The present application is a 35 U.S.C. 371 National Application of PCT/EP2010/068595 filed Dec. 1, 2010, which claims priority to European Patent Application No. 09177684.9, filed Dec. 2, 2009, the entire contents of which are incorporated entirely herein by reference.

FIELD OF THE INVENTION

The present invention relates to the field of drug delivery devices an in particular to cartridge holders of drug delivery devices such like pen-type injectors, hence to injectors of the kind that provide for administration of medicinal products by way of injection from a multi dose cartridge. Preferably, the present invention relates to such injectors, where a user may set and dispense the dose.

BACKGROUND AND PRIOR ART

User operated drug delivery devices are as such known in the prior art. They are typically applicable in circumstances, in which persons without formal medical training, i.e., patients, need to administer an accurate and predefined dose of a medicinal product, such as heparin or insulin. In particular, such devices have application, where a medicinal product is administered on a regular or irregular basis over a short term or long-term period.

In order to accommodate with these demands, such devices have to fulfill a number of requirements. First of all, the device must be robust in construction, yet easy to use in terms of handling and in understanding by the user of its operation and the delivery of the required dose or medicament. The dose setting must be easy and unambiguous. Where the device is to be disposable rather than reusable, the device should be inexpensive to manufacture and easy to dispose. Moreover, the device should be suitable for recycling. To meet these requirements, the number of parts required to assemble the device and the number of material types the device is made from need to be kept to a minimum.

The medicinal product to be dispensed by means of the drug delivery device is typically provided in a disposable or replaceable cartridge, such as a vial, an ampoule or a carpule comprising a slidably disposed piston to be operably engaged with a piston rod of the drug delivery device's drive mechanism. By applying thrust to the cartridge's piston in distal direction, a predefined dose of the liquid drug can be dispensed and expelled from the cartridge.

Cartridges as they are typically used with drug delivery devices are typically sealed by means of as sealing septum. Such a septum is commonly designed as rubber stopper providing an air-tight seal but being pierceable by piercing elements such as needles or cannulae.

A typical cartridge holder assembly 10 according to the prior art is illustrated in cross section in FIG. 1. The cartridge holder assembly 10 comprises a cartridge holder 14, 16 adapted to receive a cartridge 12, which is hermetically sealed with a flexible and deformable septum 18. At its lower and distal end section 14, the cartridge holder is threadedly engaged with a needle mount 24. Said mount or needle holder comprises a threaded cylindrical portion 24 allowing to screw the needle holder on the threaded neck portion 14 of the cartridge holder. At its lower and distal section, the mount 24 comprises a bottom portion 25, which in a concentrically inner section holds the injection needle or cannula 30.

During assembly of the needle mount 24, the proximally located tipped end of the needle 30 penetrates the septum 18. In this way, a fluid-transferring connection for the purpose of dose dispensing can be established. Additionally, the distal and free end of the needle 30 can be provided with a removable needle cap 28. Also, the entire cartridge holder assembly 10 can be covered and protected by a protective cap 26.

Depending on manufacturing tolerances and depending on the concrete design of cartridge 12 and cartridge holder 14, 16, an axial gap 22 of variable size is typically formed between the bottom portion 25 of the needle mount 24 and the distal end face of the cartridge 12. As further illustrated in FIG. 1, the needle mount 24 comprises a radially inwardly directed bottom portion 25 at its distal end, which serves as a distal end stop for the cartridge 12. With an aluminium cap 20 that fixes the septum 18 in position, the cartridge 12 buts against said bottom portion 25.

Axial size of said space 22 may vary, e.g. due to manufacturing and assembly tolerances. In particular, during dispensing of a dose of a medicinal fluid, a respective fluid pressure is built-up, which, due to the elasticity of the septum 18, may lead to a respective axial expansion of the septum 18. As a consequence, the septum 18 may at least partly extend through a through opening 23 of the aluminium cap 20. When a respective fluid pressure builts up inside the cartridge 12 the septum 18 may almost entirely fill out the space 22 between the needle holder 25 and the distal end face of the cartridge 12.

Due to its elastic properties, the septum 18 also stores elastic energy during dose dispensing. As soon as the fluid pressure returns to an initial level after termination of a dose dispensing procedure, the septum 18 relaxes to its initial configuration, which is accompanied by a retraction of the expanded section of the septum 18 back into the cartridge 12. Such retracting motion may in turn lead to a built-up of a non-negligible post-dispensing fluid pressure, and, as a consequence, a certain amount of medicinal fluid may be supplementally expelled from the cartridge 12, which can be typically observed in the form of droplet formation at the distal tip of the needle 30.

Moreover, the axial expansion of the septum 18 may also lead to a respective proximally directed axial displacement of the cartridge 12 with respect to the cartridge holder 14 and/or with respect to the housing of the drug delivery device. Additionally, the drive mechanism operably engaged with the cartridge and/or its piston may also become subject to a respective axial displacement due to manufacturing and/or assembly tolerances. Generally, any axial displacement of the cartridge and/or its septum is finally at the expense of dosing accuracy.

OBJECTS OF THE INVENTION

It is therefore an object of the present invention, to provide an improved cartridge holder for a drug delivery device, which counteracts generation of droplets after termination of a dose dispensing procedure. As a further aim, the invention focuses on improvements with respect to dosage accuracy. Furthermore, the invention aims to provide an inexpensive as well as stable and robust design of a drug delivery device.

SUMMARY OF THE INVENTION

The present invention refers to a cartridge holder for a drug delivery device, which is adapted to dispense a single or multiple doses of a medicinal product, preferably by way of injection. Hence, the cartridge holder is particularly designed for drug delivery devices such as pen-type injectors.

The cartridge is typically designed as a vial, a carpule or an ampoule. It is filled or it is to be filled with a medicinal product to be dispensed by the drug delivery device in a well-defined way, typically in multiple doses.

The cartridge typically contains a medicinal fluid, such as heparin or insulin. It is hermetically sealed by means of a flexible and deformable septum, which is penetrable by a piercing element, such like an injection needle or a cannula.

In a proximal portion, the cartridge holder receives the cartridge being filled with the medicinal fluid to be dispensed by the drug delivery device. The cartridge holder further comprises a distal portion comprising a mount for a piercing assembly. The piercing assembly, typically designed as a needle holder or needle mount, is adapted to provide a fluid-transferring connection with the inner volume of the cartridge by way of a piercing element, such like an injection needle or cannula.

The cartridge holder further comprises retaining means that are adapted to substantially prevent the cartridge at least from displacing in proximal direction with respect to the proximal portion and/or with respect to the distal portion of the cartridge holder.

By way of the retaining means, the cartridge can be axially fixed with respect to the cartridge holder and/or with respect to the housing of the drug delivery device. In this way, axial displacement of the cartridge inside the cartridge holder and/or inside the housing of the drug delivery device can be effectively counteracted or even entirely prevented. The retaining means are at least adapted to fix the cartridge in proximal direction with respect to the cartridge holder's proximal portion. The retaining means may even be adapted to fix the cartridge in distal direction with respect to the cartridge holder.

Preferably, cartridge and cartridge holder are mutually fixed in such a way, that the cartridge even under the effect of a distally directed force during dose dispensing does not move with respect to the cartridge holder.

Fixing of the cartridge in distal direction can for instance be achieved in combination with a piercing assembly to be mounted on the distal portion of the cartridge holder. For this purpose, the piercing assembly may provide a distal end stop or stop element for the cartridge when assembled with the cartridge holder.

In a preferred embodiment of the invention, the proximal portion and/or the distal portion of the cartridge holder comprise a substantially cylindrical shape. Typically, shape and geometry of the cartridge holder is adapted and corresponds to the outer shape and geometry of the cartridge to be inserted into the cartridge holder and/or into the drug delivery device, respectively.

In a further preferred embodiment, the retaining means extend radially inwardly from an inside wall of the distal portion of the cartridge holder. Position and geometry of the retaining means is preferably designed such, that the cartridge is positively or frictionally locked in position in the distal portion of the cartridge holder.

Preferably, the retaining means comprise a flexible deformable material, such as natural or synthetic rubber or a thermoplastic material with comparable elastic properties. In the course of inserting the cartridge into the cartridge holder, the retaining means may become subject to temporal or durable deformation.

In typical embodiments, the retaining means comprise radially inwardly protruding struts arranged at an inner surface of the cylindrical wall of the distal portion of the cartridge holder. Typically, the retaining means comprise numerous radially inwardly protruding struts, e.g. regularly and/or equidistantly arranged on the inner cylindrical wall of the distal portion. Typically, dimensions of the cartridge, the inner diameter of the distal portion of the cartridge holder and the radial dimensions of the radially inwardly protruding struts are designed and selected such, that insertion of a distal portion of the cartridge into the respective distal portion of the cartridge holder comes along with a deformation of the retaining means, preferably in such a way, that a radial clamping of the cartridge's distal portion and the distal portion of the cartridge holder can be achieved.

Moreover, to increase friction forces in the course of an assembly of cartridge and cartridge holder, the radially inwardly protruding retaining means of the cartridge holder may vary in shape in axial direction. Preferably, the retaining means may have a conical or wedge shape radially extending towards the distal end of the cartridge holder.

It is generally also conceivable, that the retaining means extend in axial direction such that a frictional engagement of cartridge and retaining means is attained even before the cartridge reaches its final assembly position in the cartridge holder.

According to another embodiment of the invention, the retaining means are arranged at such a distance from the cartridge holder's distal portion's free end, that corresponds to the axial dimensions of a distal neck portion of the cartridge. Hence, the cartridge at its distal end section comprises a stepped down neck portion being smaller in diameter than a residual proximal portion of the cartridge. Typically, the distal end section of the cartridge hermetically sealed by way of a septum is covered by a crimped aluminium cap, which in proximal direction ends in an indented section, coinciding for instance with the neck of the cartridge.

Since the distal portion of the cartridge comprises an indentation, the retaining means, for instance in form of radially inwardly protruding struts, are axially arranged in the region of said indentations. In this way, even a positive mutual axial interlocking of the indentation and radially inwardly protruding struts can be achieved.

In another supplemental or alternative embodiment, the retaining means comprise at least one axially and/or circumferentially extending retaining rib, arranged along the inside wall of the distal portion of the cartridge holder. Preferably, numerous ribs arranged at different circumferential and/or axial positions are provided along the inside wall of the distal portion of the cartridge holder. By means of the retaining ribs, the inner diameter of the cartridge holder's distal portion is reduced to a size being smaller than the radial dimensions of the corresponding cartridge's stepped down neck portion. In this way, the cartridge experiences radially directed clamping when inserted into the cartridge holder.

According to another embodiment, the radial distance between radially inwardly protruding retaining means, in particular of radially inwardly protruding struts and/or axially extending ribs is smaller than the radial dimensions of the distal neck portion of the cartridge. In this way, insertion of the cartridge into the cartridge holder yields to a deformation of the respective struts and/or ribs, such that a clamping effect between cartridge holder and cartridge can be attained in such a way that the cartridge is substantially fixed to cartridge holder.

In a further preferred embodiment, the distal portion of the cartridge holder comprises an outside thread, which is adapted to threadedly receive a corresponding inner thread of the piercing assembly. In this embodiment, the mount of the distal portion is designed as an outside thread and an assembly of distal portion and piercing assembly can be achieved by means of a threaded engagement.

The piercing assembly typically comprises a cupped body of substantially cylindrical shape, wherein the inner thread is provided on the inner surface of the cylindrical side wall of said body.

According to a further preferred embodiment, the distal portion of the cartridge holder comprises at least one axially extending slit, that divides the distal portion into at least two radially inwardly deformable distal segments. The axial slit also intersects the outside thread of the distal portion. Moreover, the distal segments of the cartridge holder might be subject to a radially outwardly directed pre-tension, which may facilitate insertion of the cartridge into the distal portion of the cartridge holder. By subsequently screwing the cupped piercing assembly on the distal portion of the cartridge holder, the distal segments of the cartridge holder become subject to a radially inwardly directed deformation, by way of which a mutual clamping of cartridge holder and cartridge can be established and/or further enhanced.

In a further preferred embodiment, the distal portion of the cartridge holder is opened towards its distal end. In contrast to prior art solutions, such as illustrated in FIG. 1, the distal portion of the cartridge holder according to the present invention does not comprise such radially inwardly directed flange portions. In this way, the distal end face of the cupped piercing assembly provides a distal end stop for the cartridge almost across the entire inner surface of its bottom portion, when assembled with the cartridge holder. This is of particular benefit, since the distal end face of the cartridge itself buts against a distal end stop of the needle mount or piercing assembly, respectively. By having such an abutment configuration, distally directed axial displacement of the septum can be effectively prevented and droplet generation is counteracted.

In another aspect, the distal portion of the cartridge holder is integrally formed with the proximal portion of the cartridge holder, wherein the proximal portion is larger in diameter than the distal portion. Typically, a shoulder portion extends between the proximal portion and the distal portion of the cartridge holder. The dimensions and shapes of distal—and proximal—as well as of shoulder portions of the cartridge holder are designed in such a way, that the cartridge buts against the shoulder portion of the cartridge holder when reaching its final assembly position in the cartridge holder, in which the distal end face of the cartridge is substantially surface-flushed with the distal end of the cartridge holder.

In a further independent aspect, the invention also relates to a drug delivery device for administering a dose of a medicinal product, preferably by way of injection. The drug delivery device comprises a housing and a drive mechanism, wherein the drive mechanism is to be operably engaged with a piston of a cartridge for dispensing of a pre-defined dose of a medicinal product contained in said cartridge. Furthermore, the drug delivery device is equipped with a cartridge holder according to the present invention, and with a cartridge being at least partially filled with the medicinal product and being disposed in the cartridge holder.

The term "medicament" or "medicinal product", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu- Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36[Asp28]Exendin-4(1-39),
des Pro36[IsoAsp28]Exendin-4(1-39),
des Pro36[Met(O)14, Asp28]Exendin-4(1-39),
des Pro36[Met(O)14, IsoAsp28]Exendin-4(1-39),
des Pro36[Trp(O2)25, Asp28]Exendin-4(1-39),
des Pro36[Trp(O2)25, IsoAsp28]Exendin-4(1-39),
des Pro36[Met(O)14 Trp(O2)25, Asp28]Exendin-4(1-39),
des Pro36[Met(O)14 Trp(O2)25, IsoAsp28]Exendin-4(1-39); or
des Pro36[Asp28]Exendin-4(1-39),
des Pro36[IsoAsp28]Exendin-4(1-39),
des Pro36[Met(O)14, Asp28]Exendin-4(1-39),
des Pro36[Met(O)14, IsoAsp28]Exendin-4(1-39),
des Pro36[Trp(O2)25, Asp28]Exendin-4(1-39),
des Pro36[Trp(O2)25, IsoAsp28]Exendin-4(1-39),
des Pro36[Met(O)14 Trp(O2)25, Asp28]Exendin-4(1-39),
des Pro36[Met(O)14 Trp(O2)25, IsoAsp28]Exendin-4(1-39),
wherein the group -Lys6-NH2 may be bound to the C-terminus of the Exendin-4 derivative;
or an Exendin-4 derivative of the sequence H-(Lys)6-des Pro36[Asp28]Exendin-4(1-39)-Lys6-NH2,
des Asp28 Pro36, Pro37, Pro38Exendin-4(1-39)-NH2,
H-(Lys)6-des Pro36, Pro38[Asp28]Exendin-4(1-39)-NH2,
H-Asn-(Glu)5des Pro36, Pro37, Pro38[Asp28]Exendin-4(1-39)-NH2,
des Pro36, Pro37, Pro38[Asp28]Exendin-4(1-39)-(Lys)6-NH 2,
H-(Lys)6-des Pro36, Pro37, Pro38[Asp28]Exendin-4(1-39)-(Lys)6-NH2,
H-Asn-(Glu)5-des Pro36, Pro37, Pro38[Asp28]Exendin-4 (1-39)-(Lys)6-NH2,
H-(Lys)6-des Pro36[Trp(O2)25, Asp28]Exendin-4(1-39)-Lys6-NH2,
H-des Asp28 Pro36, Pro37, Pro38[Trp(O2)25]Exendin-4(1-39)-NH2,
H-(Lys)6-des Pro36, Pro37, Pro38[Trp(O2)25, Asp28]Exendin-4(1-39)-NH2,
H-Asn-(Glu)5-des Pro36, Pro37, Pro38[Trp(O2)25, Asp28] Exendin-4(1-39)-NH2,
des Pro36, Pro37, Pro38[Trp(O2)25, Asp28]Exendin-4(1-39)-(Lys)6-NH2,
H-(Lys)6-des Pro36, Pro37, Pro38[Trp(O2)25, Asp28]Exendin-4(1-39)-(Lys)6-NH2,
H-Asn-(Glu)5-des Pro36, Pro37, Pro38[Trp(O2)25, Asp28] Exendin-4(1-39)-(Lys)6-NH2,
H-(Lys)6-des Pro36[Met(0)14, Asp28]Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38[Met(O)14, Asp28]Exendin-4(1-39)-NH2,
H-Asn-(Glu)5-des Pro36, Pro37, Pro38[Met(O)14, Asp28] Exendin-4(1-39)-NH2,
des Pro36, Pro37, Pro38[Met(O)14, Asp28]Exendin-4(1-39)-(Lys)6-NH2,
H-(Lys)6-des Pro36, Pro37, Pro38[Met(O)14, Asp28]Exendin-4(1-39)-(Lys)6-NH2,
H-Asn-(Glu)5 des Pro36, Pro37, Pro38[Met(O)14, Asp28] Exendin-4(1-39)-(Lys)6-NH2,
H-Lys6-des Pro36[Met(O)14, Trp(O2)25, Asp28]Exendin-4 (1-39)-Lys6-NH2,
H-des Asp28 Pro36, Pro37, Pro38[Met(O)14, Trp(O2)25] Exendin-4(1-39)-NH2,
H-(Lys)6-des Pro36, Pro37, Pro38[Met(O)14, Asp28]Exendin-4(1-39)-NH2,
H-Asn-(Glu)5-des Pro36, Pro37, Pro38[Met(O)14, Trp(O2) 25, Asp28]Exendin-4(1-39)-NH2,
des Pro36, Pro37, Pro38[Met(O)14, Trp(O2)25, Asp28]Exendin-4(1-39)-(Lys)6-NH2,
H-(Lys)6-des Pro36, Pro37, Pro38[Met(O)14, Trp(O2)25, Asp28]Exendin-4(S1-39)-(Lys)6-NH2,
H-Asn-(Glu)5-des Pro36, Pro37, Pro38[Met(O)14, Trp(O2) 25, Asp28]Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be apparent to those skilled in the art, that various modifications and variations can be made to the present invention without departing from its spirit and scope. Further, it is to be noted, that any reference signs used in the appended claims are not to be construed as limiting the scope of the present invention.

BRIEF DESCRIPTION OF THE DRAWINGS

Without limitation, the present invention will be explained I greater detail below in connection with preferred embodiments and with reference to the drawings in which:

FIG. 2 shows a corresponding cross-sectional view of a cartridge holder assembly according to a first embodiment of the invention, FIG. 3 illustrates a cross-sectional view of a cartridge holder assembly according to a second embodiment of the invention and FIG. 4 is illustrative of a cross-sectional view of the cartridge holder assembly according to a third embodiment of the invention.

DETAILED DESCRIPTION

Figure 1:
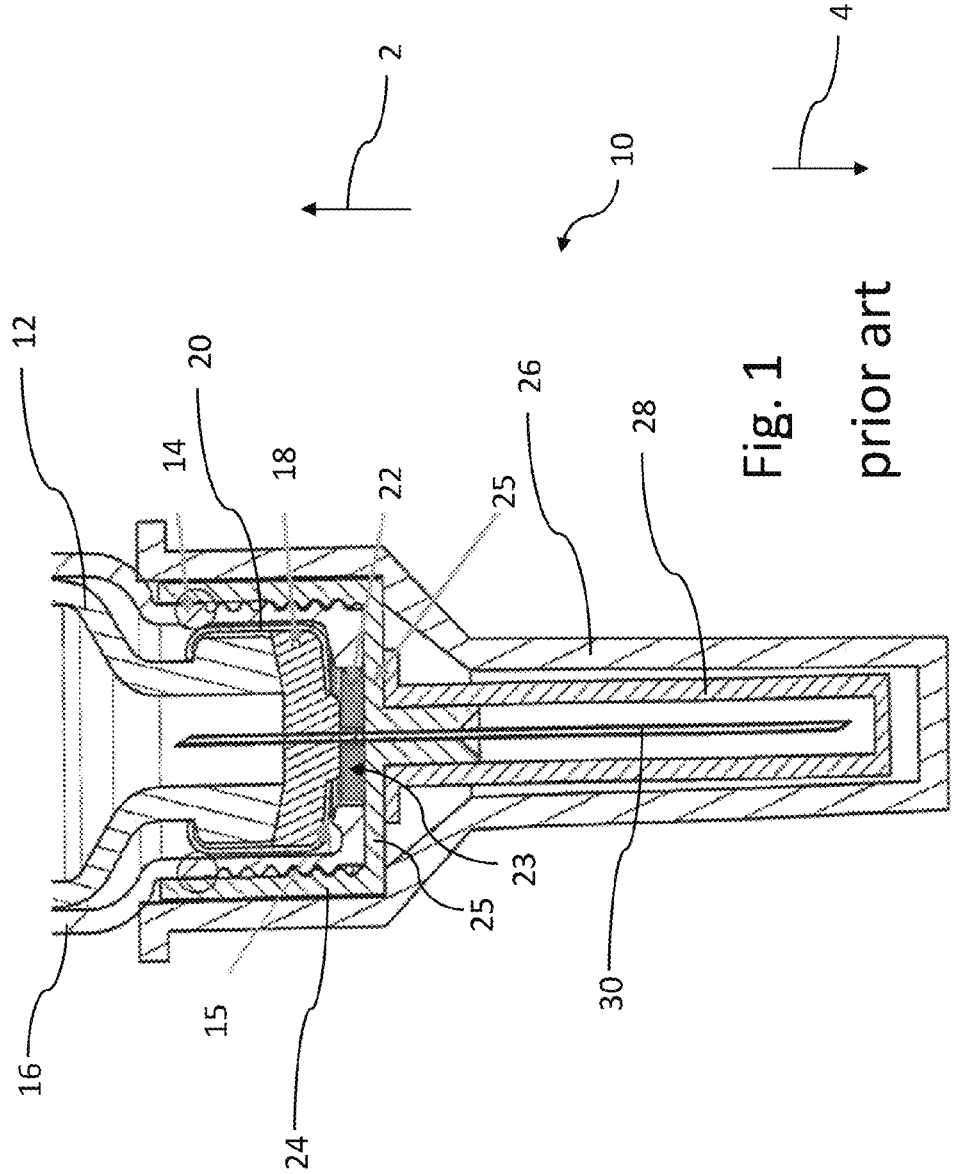
FIG. 1 schematically illustrates a cartridge holder assembly in cross-sectional view according to the prior art.

In contrast to a cartridge holder assembly 10 according to the prior art as illustrated in FIG. 1, the cartridge holders 32, 38, 48 according to the present invention as depicted in FIGS. 2 through 4 do no longer comprise a radially inwardly directed flange portion 15 at their distal end section. Hence, the cartridge holders 32, 38, 48 comprise a distal end having an inner diameter that corresponds to the outer diameter of a stepped down distal neck portion 13 of a cartridge 12 to be inserted and to be received by the respective cartridge holders 32, 38, 48.

As illustrated throughout FIGS. 1 to 4, the proximal direction is depicted with an upward pointing arrow 2 and the distal direction is indicated by a downward pointing arrow 4.

As can further be seen from the sketches of FIGS. 2 to 4 a distal portion of the aluminium cap 20 directly buts against the bottom portion 25 of the needle holder 24. Axially and distally directed expansion of the septum 18 is therefore effectively prevented. Particularly, the distal end face of the aluminium cap 20 almost entirely abuts against the inside wall of the bottom portion 25 of the needle mount 24.

Additionally and in contrast to the configuration of FIG. 1, the cartridge 12 is retained in a press fit in the cartridge holders 32, 38, 48. As illustrated in FIGS. 2 to 4, the cartridge 12 is directly supported in axial direction by means of a shoulder portion 35 extending between a stepped down distal portion 34 and a radially widened proximal portion 36 of the cartridge holder 32, 38, 48, respectively.

In this way, the cartridge 12 is secured in distal direction with respect to the cartridge holder 32, 38, 48 by way of abutment with the bottom portion 25 of the needle holder 24 as well as by means of a direct abutment with the shoulder portion 35. Mutual abutment of shoulder portion 35 and cartridge 12 is of particular benefit, because a removal of the needle mount does not affect the axial position of the cartridge 12.

Additionally, the cartridge holders 32, 38, 48 comprise retaining means 40, 42, 44, in order to prevent a distally, hence upwardly directed displacement of the cartridge 12 with respect to the cartridge holder 32, 38, 48. In the embodiment according to FIG. 2, the retaining means are configured as radially inwardly protruding struts 40, that are located at an axial distance to the distal end of the distal portion 34 of the cartridge holder 32.

Here, the axial position of the radially inwardly protruding struts 40 corresponds to a radial indentation of the distal neck portion 13 of the cartridge 12. The radially inwardly protruding struts 40 can be elastically deformed. Alternatively, they may be spring biased in radial direction, so as to allow a smooth insertion of the neck portion 13 into the respective distal portion 34 of the cartridge holder 32. However, the struts 40 serve to prevent a displacement of the cartridge in the opposite, hence axial direction.

Instead or alternative to a plurality of struts being spaced apart, also a collar-like circumferential rib can be arranged at the inside wall of the distal portion of the cartridge holder.

Moreover, the various retaining means 40, 42, 44 as illustrated in the embodiments according to FIGS. 2 to 4 may also be disposed in or at a proximally and radially widened portion 36 of the cartridge holder.

In the alternative embodiment according to FIG. 3, the retaining means 42 are designed as axially extending but radially protruding ribs, that may be arranged at a mutual distance on the inner circumference of the distal portion 34 of the cartridge holder 38. These axially elongated or axially extended ribs 42 serve to provide a clamping and support a tight fit of the cartridge 12 inside the cartridge holder 38.

In a similar way, the radially inwardly protruding struts 44 as illustrated in the embodiment according to FIG. 4 provide radial clamping of the cartridge's neck portion 13 in the cartridge holder 48. Here, the radially inwardly protruding struts 44 may extend along the entire circumference of the distal portion 34 of the cartridge holder 48. Alternatively, the retaining means 44 according to FIG. 4 comprise numerous circumferentially spaced, radially inwardly protruding and elastically deformable clamping elements.

Finally, it is to be mentioned, that the retaining means 40, 42, 44 as illustrated separately in the embodiments according to FIGS. 2 to 4 can be arbitrarily combined in order to provide sufficient axial fixing of the cartridge 12 with respect to the cartridge holders 32, 38, 48.

LIST OF REFERENCE NUMERALS 10 cartridge holder assembly
12 cartridge
13 neck portion
14 distal cartridge holder portion
15 flange portion
16 proximal cartridge holder portion
18 septum
20 aluminium cap
22 free space
23 through opening
24 needle holder
25 bottom portion
26 protective cap
28 protective cap
30 needle
32 cartridge holder
34 distal cartridge holder portion
35 shoulder portion
36 proximal cartridge holder portion
37 distal end face
40 retaining means
42 retaining means
44 retaining means

The invention claimed is:

1. A cartridge holder for a drug delivery device, which houses a cartridge having a hermetically sealed distal end section, comprising:
   a proximal portion for receiving the cartridge filled with a medicinal fluid to be dispensed by the drug delivery device,
   a distal portion comprising a mount for a piercing assembly, wherein the piercing assembly is adapted to provide a fluid-transferring connection with an inner volume of the cartridge by way of a piercing element pointing in a distal direction with a pointed free end section, and wherein the piercing assembly comprises a planar shaped bottom portion;
   wherein the distal portion is opened towards its distal end, such that the piercing assembly provides a distal end stop for the cartridge across the entire inner surface of its bottom portion when assembled with the cartridge holder,
   wherein the distal portion is void or is free of a radially inwardly directed flange portion at its distal end section;
   wherein a distal end face of the cartridge is substantially surface-flushed with a distal end of the cartridge holder, and a distal end of the cartridge almost entirely abuts against the inside of the bottom portion of the piercing assembly in order to prevent post-dispensing droplet generation;
   wherein the distal portion further comprises an outside thread adapted to threadedly receive a corresponding inner thread of the piercing assembly and
   retaining means adapted to substantially prevent the cartridge from displacing in a proximal direction with respect to the proximal portion and/or distal portion characterized in that:
   the distal portion is integrally formed with the proximal portion being larger in inner diameter than the distal portion, and
   wherein the retaining means comprise axially and/or circumferentially extending retaining ribs arranged along an inside wall of the distal portion adapted to retain the cartridge in a press-fit.

2. The cartridge holder according to claim 1, wherein the proximal portion and/or the distal portion comprise a substantially cylindrical shape.

3. The cartridge holder according to claim 1, wherein retaining means extend radially inwardly from an inside wall of the distal portion.

4. The cartridge holder according to claim 1, wherein the retaining means comprise a flexible deformable material.

5. The cartridge holder according to claim 1, wherein the retaining means comprise radially inwardly protruding struts.

6. The cartridge holder according to claim 5, wherein the retaining means are arranged at a distance from the distal portion's free end, that corresponds to the axial dimensions of a distal neck portion of the cartridge.

7. The cartridge holder according to claim 1, wherein the retaining means comprise axially and/or circumterentiany extending retaining ribs arranged along the inside wall of the distal portion.

8. The cartridge holder according to claim 1, wherein a radial distance between a radially inwardly protruding retaining means is smaller than the radial dimensions of a distal neck portion of the cartridge.

9. The cartridge holder according to claim 1, wherein the distai portion comprises an outside thread adapted to threadediy receive a corresponding inner thread of the piercing assembly.

10. The cartridge holder according to claim 1, wherein the distal portion is integrally formed with the proxiryiai portion being larger in diameter than the distal portion.

11. The cartridge holder according to claim 1, wherein a shoulder portion extends between the proximal portion and distal portion, wherein said shoulder portion provides an end stop for a corresponding shoulder of the cartridge.

12. A drug delivery device for administering a dose of a medicinal product comprising:
   a housing;
   a cartridge holder according to claim 1, and
   a cartridge at least partially filled with the medicinal product and being disposed in the cartridge holder.

* * * * *